(12) United States Patent
Mallozzi et al.

(10) Patent No.: US 11,653,891 B2
(45) Date of Patent: May 23, 2023

(54) APPARATUS AND METHOD FOR LARGE FIELD-OF-VIEW MEASUREMENTS OF GEOMETRIC DISTORTION AND SPATIAL UNIFORMITY OF SIGNALS ACQUIRED IN IMAGING SYSTEMS

(71) Applicant: THE PHANTOM LABORATORY, INCORPORATED, Greenwich, NY (US)

(72) Inventors: Richard P. Mallozzi, Middleton, MA (US); Joshua R. Levy, Salem, NY (US)

(73) Assignee: THE PHANTOM LABORATORY, INCORPORATED, Greenwich, NY (US)

( * ) Notice: Subject to any disclaimer, the term of this patent is extended or adjusted under 35 U.S.C. 154(b) by 243 days.

(21) Appl. No.: 17/214,383

(22) Filed: Mar. 26, 2021

(65) Prior Publication Data

US 2021/0212655 A1 Jul. 15, 2021

Related U.S. Application Data

(62) Division of application No. 16/721,048, filed on Dec. 19, 2019, now Pat. No. 11,064,967, which is a
(Continued)

(51) Int. Cl.
*G06T 7/80* (2017.01)
*A61B 6/00* (2006.01)
(Continued)

(52) U.S. Cl.
CPC .............. *A61B 6/583* (2013.01); *G01R 33/58* (2013.01); *G06T 7/80* (2017.01); *A61B 5/055* (2013.01);
(Continued)

(58) Field of Classification Search
CPC ........... A61B 6/583; A61B 5/055; G06T 7/80; G06T 2207/10088; G06T 2207/30208; G01R 33/58
See application file for complete search history.

(56) References Cited

U.S. PATENT DOCUMENTS 10,555,715 B2 2/2020 Mallozzi et al.
2011/0229055 A1* 9/2011 Clarke ................... A61B 6/583
382/287
(Continued)

OTHER PUBLICATIONS

Qiu, Jianfeng, et al. "Testing the quality of images for permanent magnet desktop MRI systems using specially designed phantoms." Physics in Medicine & Biology 58.24 (2013): 8677. (Year: 2013).*
(Continued)

*Primary Examiner* — Fayyaz Alam
(74) *Attorney, Agent, or Firm* — Matthew M. Hullhan; Heslin Rothenberg Farley & Mesiti PC

(57) ABSTRACT

An apparatus and method for imaging quality assessment of an imaging system employs an aggregate phantom and a processor for imaging analysis. The aggregate phantom includes a plurality of self-contained sections configured to be moved independently and re-assembled in the imaging system. Each section includes fiducial features of known relative location. The processor: quantitatively determines location of the fiducial features within an image of the aggregate phantom; compares the determined location within the image to the known relative location of the fiducial features to produce a distortion field; and distinguishes between actual geometric distortion of the imaging system and rigid-body transformations of sections of the aggregate phantom, in the distortion field. For extended fields-of-view, the aggregate phantom may be repositioned, and sets of images combined to determine a distortion field of the extended image. A method employing virtual features
(Continued)

for measuring spatial uniformity of an acquired signal, is also provided.

3 Claims, 15 Drawing Sheets

Related U.S. Application Data division of application No. 15/589,557, filed on May 8, 2017, now Pat. No. 10,555,715.

(60) Provisional application No. 62/356,332, filed on Jun. 29, 2016.

(51) Int. Cl.
   *G01R 33/58* (2006.01)
   *A61B 5/055* (2006.01)
(52) U.S. Cl.
   CPC ............ *G06T 2207/10088* (2013.01); *G06T 2207/30208* (2013.01)

(56) References Cited

U.S. PATENT DOCUMENTS

| | | | |
|---|---|---|---|
| 2013/0235969 A1* | 9/2013 | Winter | A61N 5/1079 378/4 |
| 2014/0072108 A1 | 3/2014 | Rohler et al. | |
| 2014/0266198 A1* | 9/2014 | Tadic | G01R 33/56572 324/309 |
| 2015/0088449 A1* | 3/2015 | Foxall | G01R 33/30 324/307 |
| 2015/0309149 A1* | 10/2015 | Holdsworth | A61B 6/466 324/309 |
| 2015/0362575 A1* | 12/2015 | Ourselin | G06T 7/0014 382/131 |
| 2016/0203599 A1* | 7/2016 | Gillies | A61B 5/7271 382/132 |
| 2017/0100202 A1* | 4/2017 | Nemanic | A61B 90/39 |
| 2018/0005401 A1 | 1/2018 | Mallozzi et al. | |
| 2018/0031653 A1* | 2/2018 | Boernert | G01R 33/58 |
| 2018/0140272 A1* | 5/2018 | Ruchala | A61B 6/032 |
| 2018/0238988 A1* | 8/2018 | Bernstein | G01R 33/561 |
| 2020/0121276 A1 | 4/2020 | Mallozzi et al. | |

OTHER PUBLICATIONS

Hariharan, Prasanna, Melanie Freed, and Matthew R. Myers. "Use of computational fluid dynamics in the design of dynamic contrast enhanced imaging phantoms." Physics in Medicine & Biology 58.18 (2013): 6369. (Year: 2013).*
Bodurka, Jerzy, et al. "Mapping the MRI voxel volume in which thermal noise matches physiological noise—implications for fMRI." Neuroimage 34.2 (2007): 542-549. (Year: 2007).*
Illerstam, Fredrik. "Quality assurance of the spatial accuracy of large field of view magnetic resonance imaging." (2014). (Year: 2014).*
Notice of Allowance in U.S. Appl. No. 16/721,048 dated Apr. 14, 2021, 15 pgs.
The Phantom Laboratory, Magphan MR Distortion Phantoms (ADNI), Magphan Quantitative Imaging Phantom, printout available online on Feb. 23, 2017 at: https://www.phantomlab.com/magphan-adni, 3 pages.
Modus QA, A novel method for quantifying 3D geometric distortion in MRI, printout available online on Feb. 23, 2017 at: http://modusqa.com/mri/mrid3d, 12 pages.
Notice of Allowance in U.S. Appl. No. 15/589,557 dated Oct. 7, 2019, 14 pgs.
Restriction Requirement in U.S. Appl. No. 15/589,557 dated Jul. 9, 2019, 6 pgs.
Restriction Requirement in U.S. Appl. No. 16/721,048 dated Mar. 16, 2021, 7 pgs.

* cited by examiner

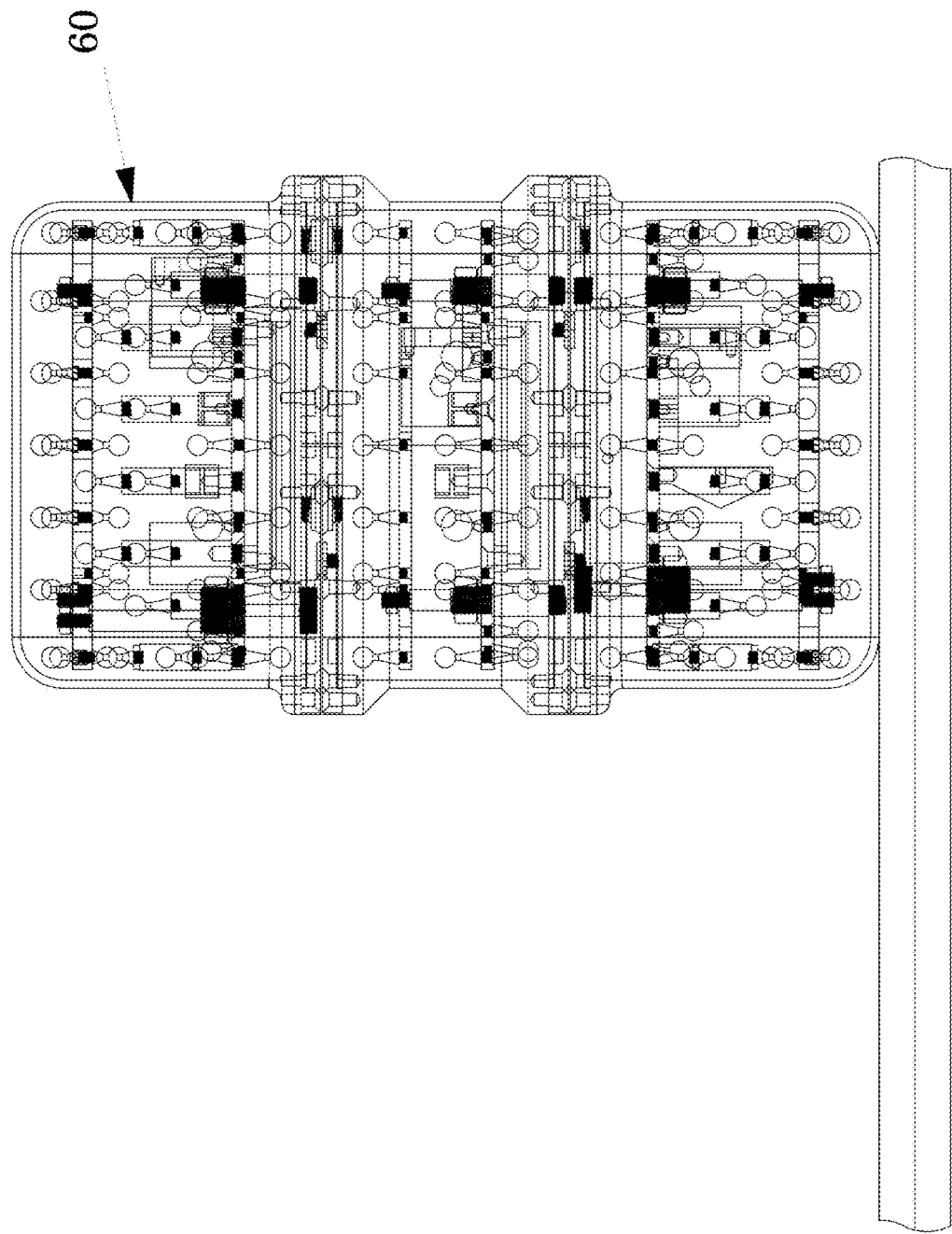

APPARATUS AND METHOD FOR LARGE FIELD-OF-VIEW MEASUREMENTS OF GEOMETRIC DISTORTION AND SPATIAL UNIFORMITY OF SIGNALS ACQUIRED IN IMAGING SYSTEMS

CROSS-REFERENCE TO RELATED APPLICATION

This application claims priority to U.S. patent application Ser. No. 16/721,048, filed on Dec. 19, 2019, which claims priority to U.S. patent application Ser. No. 15/589,557, filed on May 8, 2017, which claims priority to U.S. Provisional Application No. 62/356,332, filed on Jun. 29, 2016. The contents of the foregoing applications are hereby incorporated herein by reference in their entirety.

FIELD OF THE INVENTION

This invention relates, in general, to an apparatus and method for evaluating performance of an imaging system or scanner and, more particularly, to an aggregate phantom and analysis method especially useful for large field-of-view measurements in an MRI scanner or other imaging system.

BACKGROUND ART

Recent developments in the field of radiation therapy have enabled increasingly precise control of the applied radiation dose. Dose profiles can fall off very rapidly over distances on the millimeter scale, enabling therapy to be applied close to critical anatomy, while subjecting such anatomy to acceptably low radiation exposure. This increased control of the applied dose has motivated increased attention to the digital imaging systems used to plan the therapy.

Magnetic resonance imaging (MM) is of increasing interest for radiation therapy planning because it provides superior soft-tissue contrast to CT, enabling better visualization of pathological tissue relative to the healthy tissue. MRI, however, suffers from lower quantitative accuracy relative to CT, particularly in the area of geometric distortions. MR images have distortions that commonly reach several millimeters in magnitude.

It is possible to measure such distortions using phantoms and image analysis. Such techniques have been applied for many years over volumes pertinent to neurological scanning, using a Magphan® quantitative imaging phantom available from the Phantom Laboratory, Incorporated, located in Salem, N.Y. This phantom includes a large number of fiducial objects (markers or features) that can be located accurately within an image. Plastic spheres of 1-1.5 cm diameter are typically used as the fiducial objects. The relative location of each fiducial object is known ahead of time based on the design of the phantom, and that known location can be compared to the measured location of each fiducial object in the image. The difference characterizes the distortion throughout the volume covered by the fiducial objects.

A major challenge, however, is to perform such measurements over large, 3D fields of view that are pertinent to body imaging. A phantom large enough to cover such fields of view can weigh more than 100 pounds (45 kilograms), making it difficult to use in a clinical environment. The high weight is driven by the large volume and the need to fill the phantom with liquid in order to generate an MR signal. Classically, this is done with a very large phantom which can weigh over 100 pounds.

Others have addressed this challenge by applying a mathematical result that enables characterization of the geometric distortion throughout a volume based only on measurements of the distortion on a surface that surrounds the volume. This solution has several practical shortcomings:

1. The phantom is still heavy, presenting a challenge for safe handling by a wide range of clinical personnel.
2. The high weight of the phantom makes it difficult to add additional measurements beyond distortion, as this would further increase the weight. The currently available product performs only distortion measurements.
3. The measurements are performed with a pre-determined set of MRI pulse sequences, and do not always characterize the distortion that pertains to a specific pulse sequence used during clinical imaging.

An alternative solution, not previously applied to this problem, is to construct the phantom of multiple, self-contained sections that are moved separately and reassembled on the imaging system patient table. Once reassembled, the sections are meant to function collectively as a single large phantom assembly or aggregate phantom.

A concern with this approach, however, is achieving the tight tolerances on the geometry of the assembled phantom sections. An accuracy of 0.5 millimeters or better is desired for the distortion measurements. It is extremely difficult to control the precision of the location of each phantom section relative to the other sections with such accuracy while enabling it to be re-assembled easily by the user. Further complicating the task, is the severe restriction on acceptable materials that can be used inside an MRI scanner to avoid safety issues and imaging artifacts.

Accordingly, there is a need for a practical method and apparatus to measure, with precision, geometric distortion of an imaging system, over large, 3D fields of view.

Maintaining acceptable levels of distortion in an MR scanner relies on properly controlling many conditions. It is critical to have a robust system of quality control for key imaging performance characteristics in order to detect significant deviations before they affect clinical operations.

Although an aggregate phantom may cover a large field-of-view, it may still not cover the entire field-of-view that may be of interest for some applications. Accordingly, there is a need for a technique to cover an entire field-of-view with a phantom that encompasses less than the entire field of view.

One common measurement performed on imaging systems is the spatial uniformity of the signal acquired. Uniformity can be a useful indicator for common failure mechanisms in subsystems such as an RF coil. The uniformity is usually measured by creating a large, uniform region of a phantom and studying the variation of the signal in an image of the uniform region. There are two common configurations used for this measurement:

1. A uniform region that covers only a single or a very small number (2 or 3) slices, and is oriented only in one direction, i.e., the measurement will support only slices oriented in one direction. In some imaging systems such as MRI, slices can be acquired in any orientation and so such a limitation is undesirable.
2. A phantom, often large, consisting of a uniform fill with no other features inside.

There are also phantoms made of multiple sections, each with nothing inside except background fill. An assumption made in using such phantoms is that the fill in each section is the same as in all the other sections. This assumption can be unsettling, particularly for MRI, where the fill is fluid and the chemical properties can change over time.

Accordingly, there is also a need for an apparatus and method for measuring spatial uniformity of a signal acquired by an imaging system while compensating for signal differences attributable to different compositions or properties of different sections of a phantom.

BRIEF SUMMARY OF THE INVENTION

To address and overcome the above-noted problems, an aggregate phantom or phantom assembly composed of multiple, individual, self-contained sections or compartments that fit together and each have fiducial features at known relative locations, is provided by the present invention.

To measure and compensate for any imprecision in the location and/orientation of the individual sections relative to one another in the aggregate phantom, an analysis method is provided, preferably employing spheres as fiducial features, to determine the orientation of the phantom sections in an image. The data from the sample sections is then combined, preferably using mathematical analysis, into a single data set that covers a field-of-view. The analysis method provides a map of the geometric distortion over the entire 3D volume covered by the multitude of individual sections. The aggregate phantom and analysis method is particularly useful in measuring geometric distortion.

A novel aspect of the analysis method is the determination, from the fiducial features in the individual sections, of residual imperfections in the location and/or orientation of each individual section of the aggregate phantom. Such imperfections may be due to limitations in the precision of the manufacturing or assembling process. The analysis method of the present invention facilitates resolution of positional imperfections in the placement of each individual section of the aggregate phantom, and distinguishes between a physical displacement component attributable to such positional imperfections and actual geometric distortion of the imaging system.

The analysis method can determine these residual imperfections in a number of different ways.

One approach is to use a small number (such as 3-10) of "landmark features" or fiducials to identify each individual section, and from the positions of the landmark features determine the position and orientation of the individuals sections within the aggregate phantom.

An alternative approach is to include in the calculation of the distortion field, mathematic terms that apply a translation and a rotation in three dimensions, and perform an optimization calculation to best fit the distortions to a set of basis functions appropriate to describing the distortion field. Some examples include polynomials, spherical harmonics, and trigonometric functions. It will be appreciated by those skilled in the art that many possible basis function sets might be appropriate. The basis set is modified to include and separately identify functions that apply positional offsets due to independent translation and rotation of each individual section.

The analysis method of the present invention facilitates use of an aggregate phantom with multiple, separate, self-contained compartments or sections, which may be readily, independently transported and re-assembled within the imaging system, and facilitates integration of the imaging data into one large data set to measure, with precision, distortions over a field-of-view which encompasses all of the individual compartments or sections.

The aggregate phantom of the present invention may cover a large field-of-view, but may not cover the entire field-of-view that may of interest for certain applications. In such circumstances, an analysis technique may be employed that takes, as inputs, sets of images with the aggregate phantom (or a standard phantom) scanned in different locations within the imaging system or scanner. In this method, the aggregate phantom is scanned in an initial position and then moved to one or more new locations such that the volume covered by the image scans cover the entire field-of-view of interest. The multiple image scans may or may not overlap. The analysis method then combines these data sets using methods similar to those applied for combining the different individual sections in the aggregate phantom to provide measurements covering the entire field-of-view that is covered by the multiple scans.

According to the present invention, apparatus for image quality assessment of an imaging system, may comprise: an aggregate phantom having a plurality of self-contained sections configured to be moved independently and re-assembled in the imaging system, each section including fiducial features of known relative location, and a processor for image analysis configured for: quantitatively determining location of the fiducial features within an image, produced by the imaging system, of the aggregate phantom; comparing the determined location within the image to the known relative location of the fiducial features to produce a distortion field; and distinguishing between actual geometric distortion of the imaging system and rigid-body transformations of sections of the aggregate phantom, in the distortion field.

The distinguishing may comprise: identifying and quantifying the displacement components attributable to the rigid-body transformations of individual sections of the aggregate phantom, and determining the geometric distortion over a field of view covered by more than one section of the phantom by removing the displacement components from the distortion field.

The distinguishing may further comprise: fitting a smooth function to the distortion field, augmenting or modifying the smooth functions to include functions that characterize the rigid-body transformations of individual sections of the aggregate phantom to produce an augmented or modified set, and determining coefficients of the augmented or modified set.

The fitting may comprise: using, as a basis, at least one of polynomials, spherical harmonics, or another set of distinct functions with spatial characteristics for fitting slowly-varying functions, and determining a least-squares fitting of the coefficients.

Each self-contained section may advantageously include a uniform background liquid.

The fiducial features may advantageously comprise spheres.

The plurality of self-contained sections may comprise at least two adjacent, adjoining, contiguous, stacked or side-by-side sections.

In another aspect, at least one of the plurality of self-contained sections may include at least one additional feature for measuring an additional characteristic of the imaging system.

The additional characteristic may comprise at least one of: slice thickness, spatial resolution, spatial uniformity of a signal acquired by the imaging system, ghosting, and signal-to-noise ratio. Ghosting is when dim copies of some portion of an image appear elsewhere in the image.

When the additional characteristic comprises spatial uniformity of a signal acquired by the imaging system, a plurality of virtual features is attributed to each section of the aggregate phantom at specified locations containing only background liquid, and the processor may further: measure average values within regions of the image corresponding to the virtual features; interpolate between the average values to determine spatial uniformity of a signal acquired by the imaging system, throughout a measurement volume of the phantom; and compensate for any differences in composition between the sections of the aggregate phantom in determining the spatial uniformity of the acquired signal throughout the measurement volume. The virtual features are theoretical constructs rather than true physical structures.

The imaging system may comprise a magnetic resonance imaging system, or other imaging system.

In another aspect, a method for image quality assessment of an imaging system, may comprise: locating, within the imaging system, an aggregate phantom having multiple self-contained sections, each section including fiducial features of known relative location; creating an image of the aggregate phantom with the imaging system; and, with a processor: quantitatively determining location of the fiducial features within the image, comparing the determined location within the image to the known relative location of the fiducial features to produce a distortion field, and distinguishing between actual geometric distortion of the imaging system and rigid-body transformations of the sections of the aggregate phantom, in the distortion field.

According to this method, the distinguishing may comprise, with the processor: identifying and quantifying a displacement component attributable to rigid-body transformations of the sections of the aggregate phantom; and determining geometric distortion over a field of view covered by more than one section of the phantom by removing the displacement component from the distortion field.

The method may further comprise: determining the known location of the fiducial features by measurements on an alternative imaging system or from design and construction of the sections of the aggregate phantom.

In a further aspect, the method may further comprise: including, in at least one of the self-contained sections, at least one additional feature for measuring an additional characteristic of the imaging system.

When the additional characteristic comprises spatial uniformity of a signal acquired by the imaging system, a plurality of virtual features is attributed to each section of the aggregate phantom at specified locations containing only background liquid, and the processor may further: measure average values within regions of the image corresponding to the virtual features; interpolate between the average values to determine spatial uniformity of a signal acquired by the imaging system, throughout a measurement volume of the phantom; and compensate for any differences in composition between the sections of the aggregate phantom in determining the spatial uniformity throughout the measurement volume.

In yet another aspect, a method for performing distortion measurements of an imaging system with a phantom over a field of view larger than an imaging volume of the phantom, may comprise: acquiring a set of images, with the imaging system, of the phantom positioned at multiple locations within the field of view; combining the set of images to form an extended image; determining a distortion field of the extended image; and distinguishing between actual geometric distortion of the imaging system and rigid-body transformations attributable to repositioning of the phantom, in the distortion field.

According to this method, the phantom may comprise an aggregate phantom having multiple self-contained sections, each section including fiducial features of known relative location, and the distinguishing may include distinguishing between the actual geometric distortion of the imaging system and rigid-body transformations of the sections of the aggregate phantom, in the distortion field.

In a further aspect, a method for measuring spatial uniformity of a signal acquired by an imaging system, may comprise: locating a phantom within the imaging system; attributing virtual features to regions at known locations throughout a measurement volume of the phantom, each region containing only background liquid; imaging the phantom with the imaging system; and, with a processor: measuring average signals within the regions, and interpolating between the average signals to determine spatial uniformity of a signal acquired by the imaging system, throughout a measurement volume of the phantom.

In this method, the phantom may comprise an aggregate phantom having a plurality of self-contained sections, the locating may comprise separately transporting and re-assembling the sections within the imaging system, the attributing may comprise attributing the virtual features to regions in each section, and the processor may further compensate for any differences in composition between the sections of the aggregate phantom in determining the signal uniformity throughout the measurement volume.

Each virtual feature may have a spherical or other shape.

BRIEF DESCRIPTION OF THE DRAWING FIGURES

Details of preferred embodiments of the invention will be presented in conjunction with the accompanying drawings, in which:

FIGS. 12A-D depicts the creation of an extended image by repositioning of an aggregate phantom.

DETAILED DESCRIPTION

Figure 1:
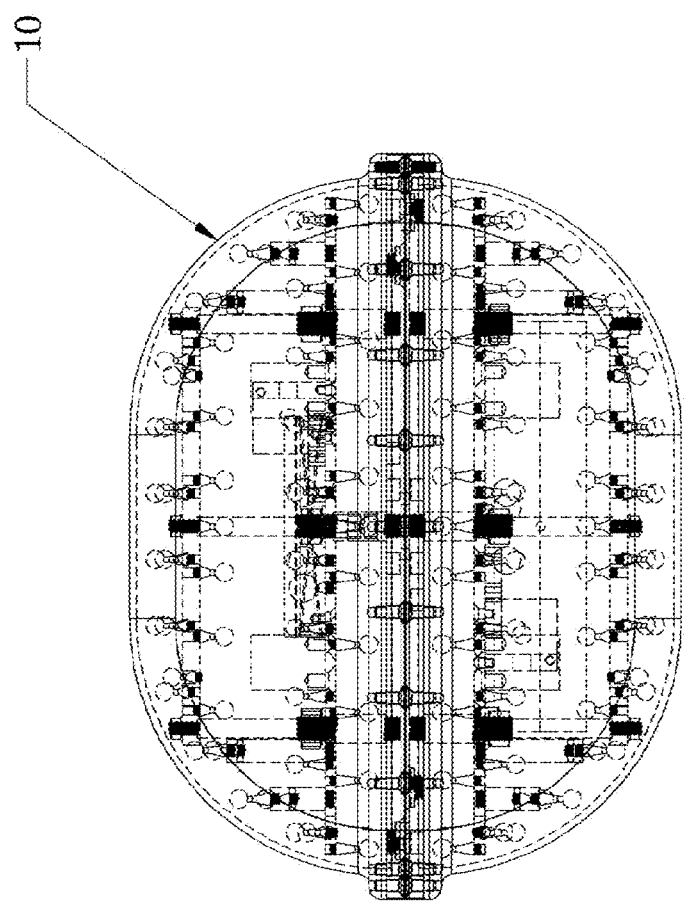
FIG. 1 is a sectional view from the side of a first embodiment of an aggregate phantom of the present invention.

This invention involves an analysis that distinguishes rigid-body transformations of phantom sections from an actual geometric distortion of the imaging system being studied. An analysis that can make such a distinction enables a phantom to be constructed out of multiple sections which, in turn, enables each section to be light enough to be moved safely in clinical environments.

Each section of an aggregate phantom can be "off" by a translation and a rotation (collectively referred to herein as a "rigid-body transformation") relative to other sections. Any errors could be interpreted as a geometric distortion instead of a phantom tolerance or displacement. Therefore, in order to use such a phantom, a technique is provided to distinguish real geometric distortions from rigid-body transformations of each section of the aggregate phantom.

This distinction is made by taking advantage of the nature of geometric distortions. Geometric distortions are relatively slowly-varying functions, and can be fit to a variety of mathematical functions such as low-order polynomials. Typically, polynomials of order three to ten in each dimension are adequate to characterize the distortion accurately.

A rigid-body transformation has a distinctive spatial characteristic. All of the fiducial markers within one section move in tandem to the same rigid-body transformation. Fiducials in a different section move to a different rigid-body transformation. Since geometric distortions ultimately originate from deviations of the magnetic fields in the scanner, no physically-realizable distortion would have such a spatial characteristic.

This distinctiveness gives rise to the analysis method of the present invention that identifies and quantifies the rigid-body transformations. After first measuring the locations of each of the fiducial markers, a fit is performed to a function that includes not only the functions used to fit the true geometric distortion, but is also augmented by functions that characterize separate rigid-body transformations of each section of the phantom. The original basis set may be further modified to identify a subset of the basis functions that describe only translations and rotations of the individual sections. The coefficients of this fit can be used to separate out the rigid-body transformations of phantom sections from true geometric distortion of the image.

Once such a distinction is made, an aggregate phantom can be built out of several, light-weight sections, enabling large field-of-view coverage with a multi-section phantom that can be transported, and handled, section by section, and then re-assembled on site. A related benefit of high commercial significance is that such a phantom can also have other features in it that perform additional measurements of the scanner or imaging system. Other important measurements such as slice thickness, spatial resolution, spatial uniformity of a signal acquired by the imaging system, signal-to-noise ratio, etc. may thus be performed with the same aggregate phantom used to measure geometric distortion.

Figure 2:
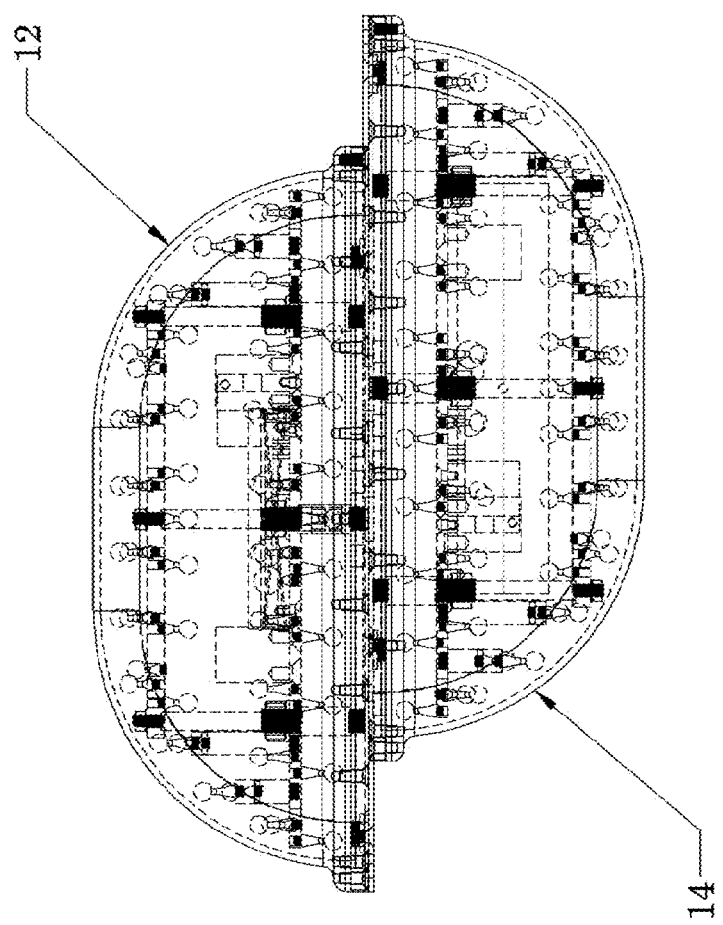
FIG. 2 is a view illustrating the two separate, self-contained sections of the aggregate phantom of FIG. 1.

An aggregate phantom 10, comprised of two separate, independently transportable, self-contained sections 12, 14, is illustrated in FIGS. 1, 2 and 3A-C. FIG. 2 shows the multiple sections prior to their reassembly as the single aggregate phantom illustrated in FIG. 3A.

The multiple sections of the aggregate phantom may be positioned adjacent, or adjoining, or contiguous, or stacked, or in a side-by-side relationship.

The individual sections are of relatively low weight, e.g. each under 12 kilograms, and can be easily transported separately, and have features that help position them accurately relative to one another.

Each self-contained section may be filled with a uniform background fluid or liquid 16, e.g., a copper sulfate and water solution that produces a bright signal in an MR image. The sections may also contain a large number (approximately 200-300) fiducial features or markers in the form of 1-cm plastic (e.g., polycarbonate) spheres 18, at known relative locations. These spheres appear dark in an MR image. This specific choice of sphere size enables a highly-precise determination of the position of the spheres within the image, to approximately 20% of the dimension of the voxels in the image. Spheres of other sizes and/or materials compatible with the imaging modality may be employed.

The fiducial features may take other shapes and forms. In addition, each section may also contain other features used to perform different measurements pertinent to the imaging scanner or system, as more fully described hereinafter.

Some fiducial markers 20 within the phantom sections are distinctive in appearance from the others, and are used to provide a preliminary position and orientation determination of the section of the phantom. These landmark fiducial markers may, for example, comprise 1.5-cm diameter spheres, while the rest of the fiducial features are 1.0-cm diameter spheres.

Figure 3B:
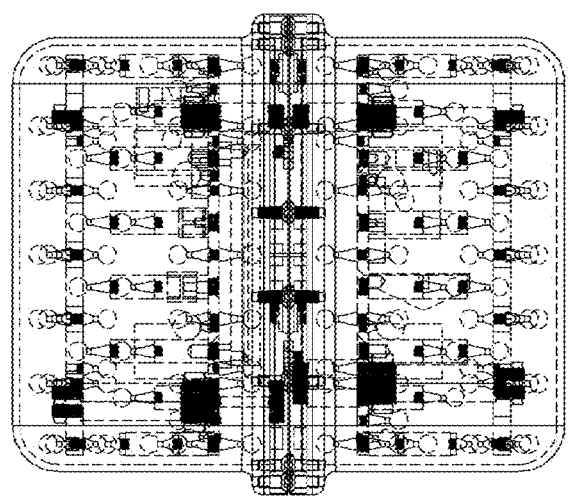
FIG. 3B is a sectional view from the front of the aggregate phantom.
Figure 3A:
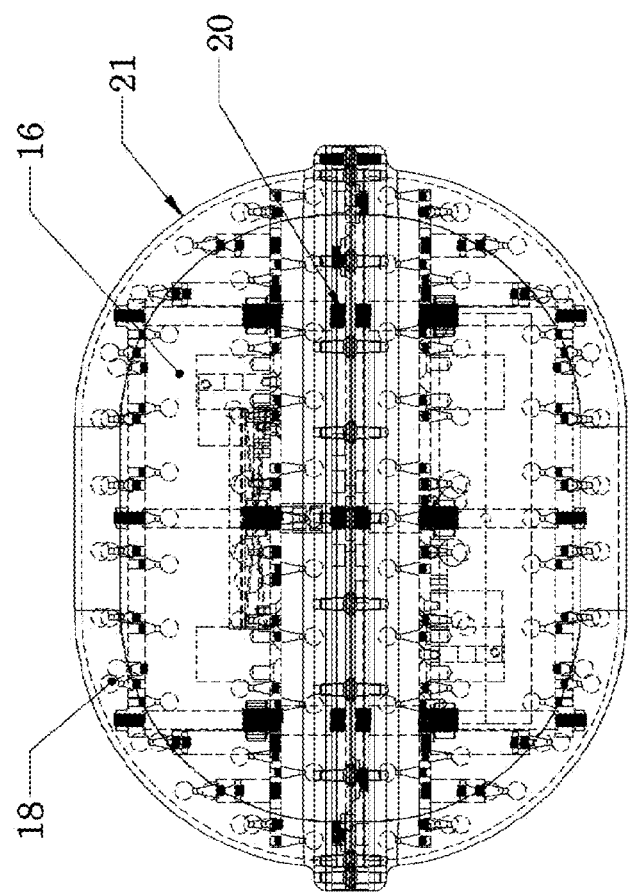
FIG. 3A is a view of the two sections assembled as an aggregate phantom.
Figure 3C:
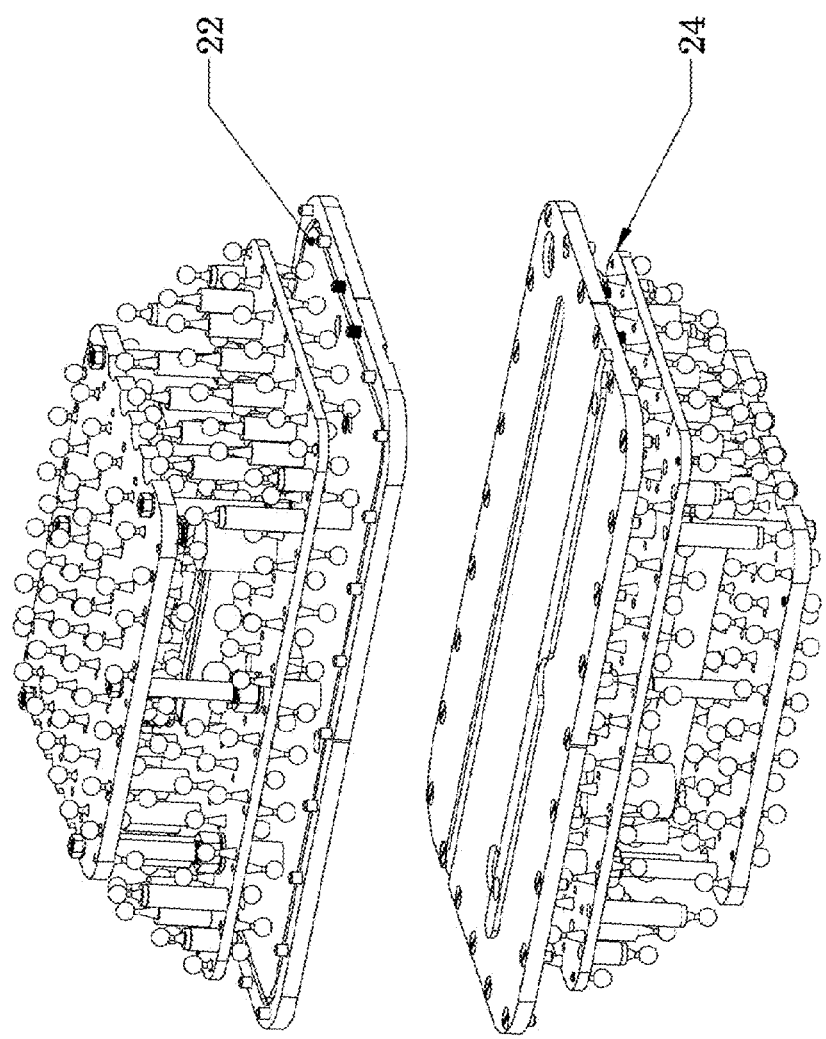
FIG. 3C depicts the interior structure of the two sections of the aggregate phantom including location of fiducial features of the aggregate phantom.
Figure 4:
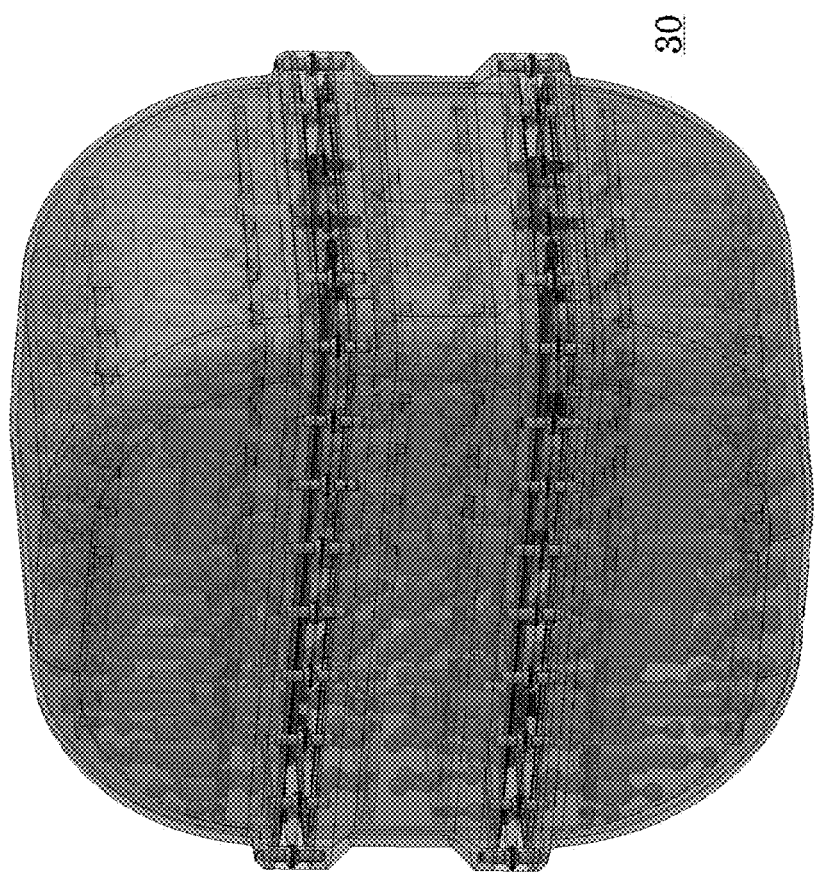
FIG. 4 depicts a second embodiment of an aggregate phantom of the present invention.
Figure 5:
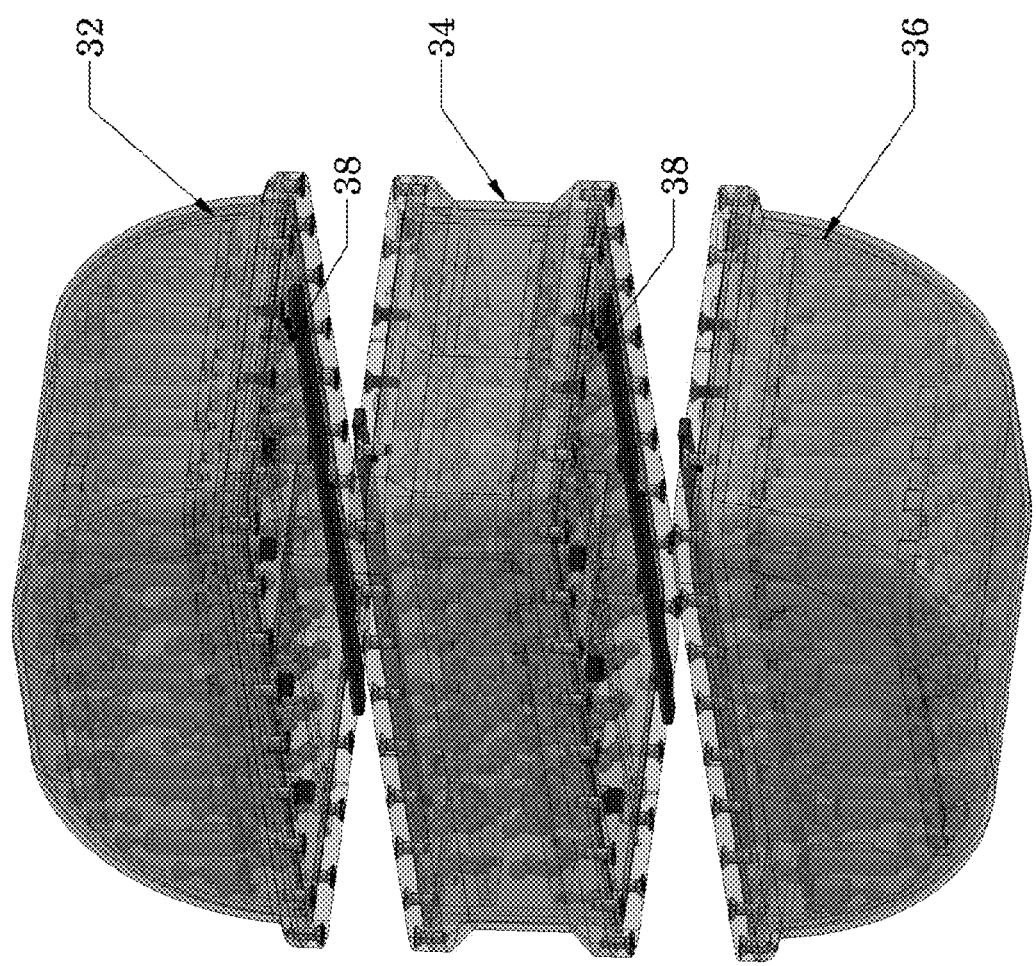
FIG. 5 illustrates the three, self-contained sections of the aggregate phantom of FIG. 4.
Figure 6B:
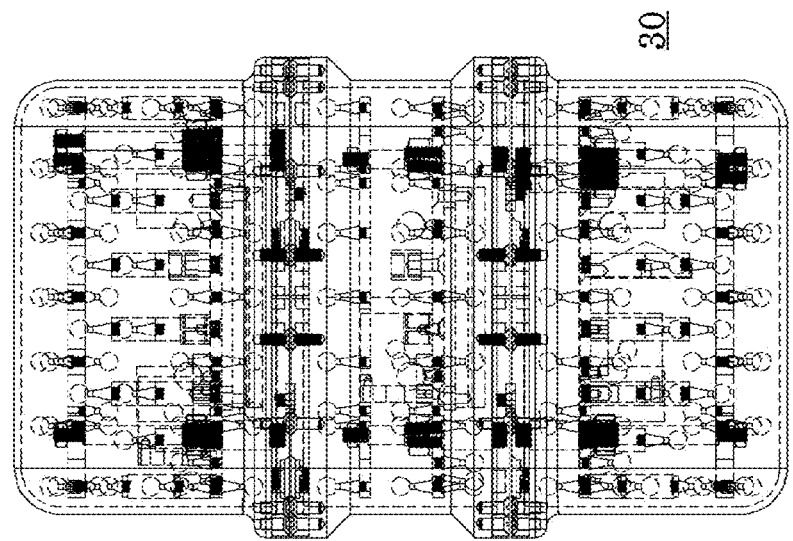
FIG. 6B is a sectional view from an end of the aggregate phantom of FIG. 6A.
Figure 6A:
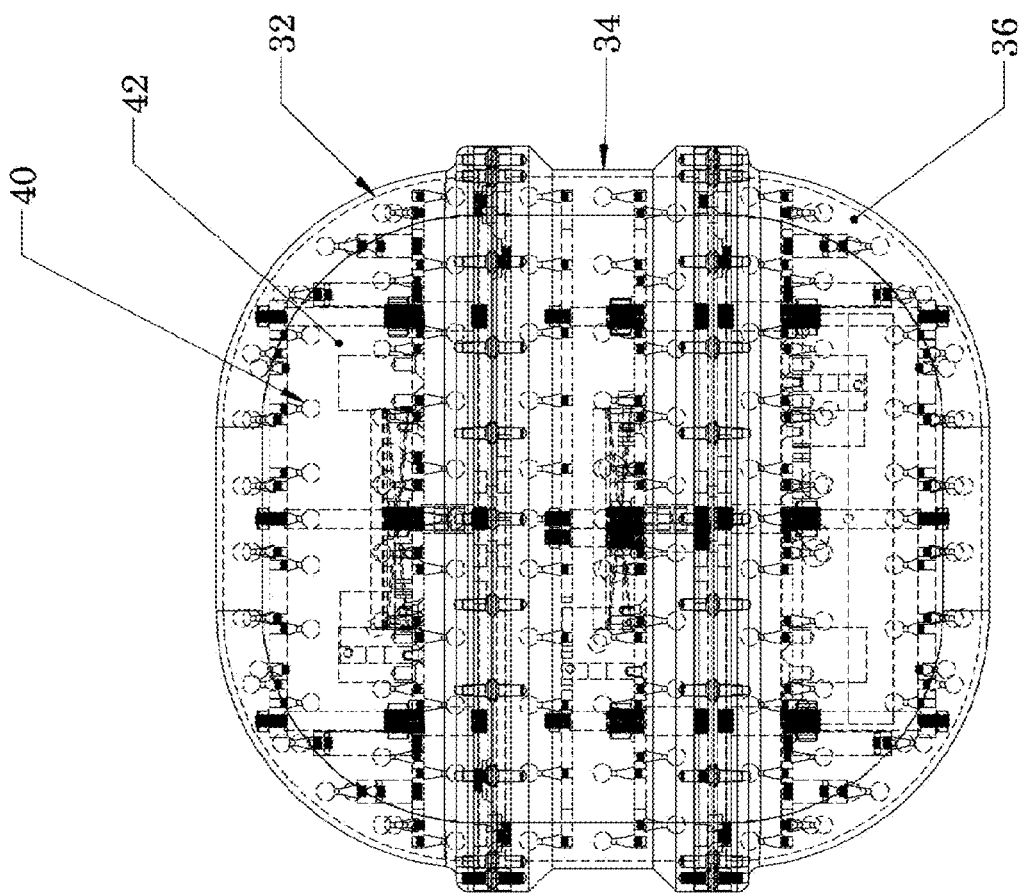
FIG. 6A is a sectional view from the side of the aggregate phantom of FIGS. 4 and 5.

The spheres or other fiducial features may be supported in each section by any appropriate support structure. Examples of such support structures 22, 24 are illustrated in FIG. 3C, and may include, for example, a series of polycarbonate plates and posts to maintain the fiducial features in fixed known relative locations within the section.

Each section of the aggregate phantom may have a housing 21, cast or otherwise formed, for example, from a clear urethane material. The housing fully encloses the support structure, fiducial features, other features, and background fill or fluid of the section, rendering each section self-contained.

The shape, size, construction, location and material of the housings may vary from that illustrated, as may the configuration, construction and material of the support structures.

By combining multiple, independently transportable, self-contained phantom sections into one aggregate phantom, a large field-of-view may be covered, while avoiding excess weight. The sections of the aggregate phantom of the present invention can be individually transported and handled, and then can be reassembled on the patient table of the imaging system. Once reassembled, the sections are meant to function collectively as a single large aggregate phantom.

FIGS. 4, 5, 6A and 6B illustrate a second embodiment of an aggregate phantom 30 of the current invention. Aggregate phantom 30 includes three sections: a top section 32, a middle section 34 and a bottom section 36. Again, each section is independently transportable and self-contained. The three sections may be initially aligned using landmark fiducial features 38 to form the aggregate phantom 30 illustrated in FIG. 4. As shown in the sectional views of FIGS. 6A-B, each section of aggregate phantom 30, in addition to the landmark fiducial features, may include a large number of other fiducial features 40, at known relative locations, for use in measuring geometric distortion of the imaging system.

The fiducial features and landmark fiducial features of aggregate phantom 30 may be similar to, or different than, the corresponding features of aggregate phantom 10. Again, each section of aggregate phantom 30 may be filled with a uniform background fluid 42 that provides a bright signal in an MR image.

The two section aggregate phantom 10 may, for example, measure geometric distortion over a 35×27×21 cm volume. The three section aggregate phantom 30 may cover a larger field-of-view than the two section version 10, while still avoiding the problem of excess weight. The higher the number of sections, the greater the modularity and configurational variations of the aggregate phantom.

The number, size, shape, and relative positioning of the sections of the aggregate phantom may vary from that shown. Although particularly beneficial for determining geometric distortion and other characteristics of an MRI imaging system, the aggregate phantom of the present invention may be used with other imaging equipment and modalities.

Similarly, the distribution, location, number, shape, material and size of the fiducial features may vary from that illustrated, provided that the fiducial features are sufficient to measure geometric distortion of the imaging system over the desired field-of-view.

Accuracy of 0.5 millimeters, or better, is desired for geometric distortion measurements of the imaging system. This imposes tight tolerances on the geometry of the assembled phantom sections.

It is extremely difficult to control the precision of the location of each phantom section relative to the other sections with such accuracy while enabling the aggregate phantom to be re-assembled easily by the user. Further complicating the task, is the severe restriction on materials acceptable for use inside an MRI scanner to avoid safety issues and imaging artifacts.

Each section of the aggregate phantom can be "off", i.e., displaced, by a translation and a rotation (collectively referred to herein as a "rigid-body transformation") relative to other sections. Any such positioning errors might be interpreted as a geometric distortion instead of a section displacement. Therefore, a technique is provided to distinguish real geometric distortions of the imaging system from rigid-body transformations of each section of the aggregate phantom.

Figure 7:
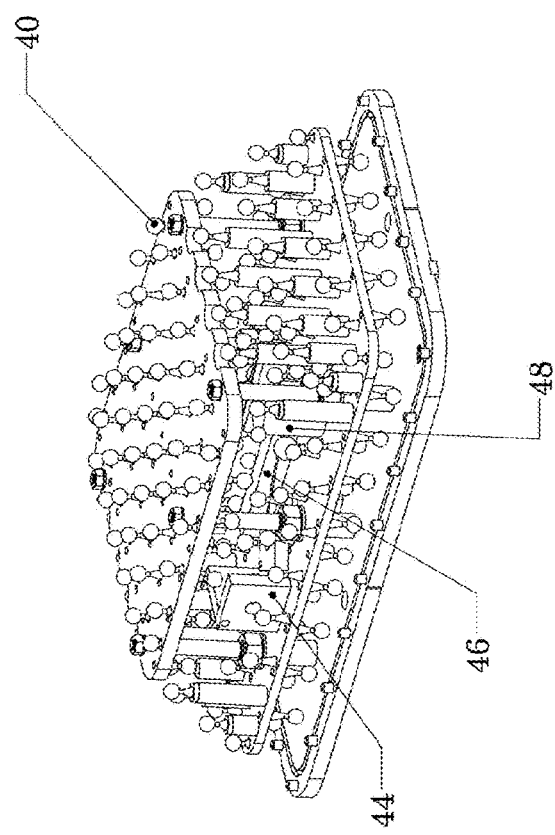
FIG. 7 depicts the inclusion of additional features in a phantom section to measure additional characteristics of an imaging system.

Once such a distinction is made, aggregate phantoms can be build out of several sections, enabling large field-of-view coverage with a phantom that is still readily handled. A related benefit of high commercial importance is that such an aggregate phantom can also have other features in it that perform additional measurements of the imaging system. Such measurements may include slice thickness, spatial resolution, spatial uniformity of the signal acquired by the imaging system, signal-to-noise ratio, etc. FIG. 7 schematically illustrates the inclusion of such additional features 44, 46, 48 among fiducial features 40 of a section of an aggregate phantom.

In a single-section phantom, the geometric distortion field may be determined by measuring the location of each fiducial marker in the image of the phantom relative to its known position within the phantom. A smooth function may be fit to the distortion field using common mathematical functions as a basis, such as polynomials, spherical, harmonics or any set of distinct functions with spatial characteristics appropriate for fitting slowly-varying functions.

The coefficients of the fit can be determined in a large variety of ways. A least-squares fit of the coefficients is currently preferred. However, different and/or more complicated fitting functions could also be used that would employ different fitting techniques.

For the multi-section aggregate phantoms of the present invention, the set of functions used to fit the distortion field is augmented with functions that are nonzero only within one section of the phantom. For example, to characterize a rigid-body transformation of one section, six such basis functions are required: three translational basis functions and three rotational basis functions. For N sections, there are 3N basis functions attributable to rigid-body transformations of the sections.

In the presently preferred embodiment, a least-squares fit is performed using the augmented set of functions as the basis set. A displacement component that arises from the 3N rigid-body basis functions, is removed from the total measured distortion, and the remainder comprises the real geometric distortion of the imaging system.

One common measurement performed on imaging systems is the spatial uniformity of the signal acquired by the imaging system. Uniformity can be a useful indicator for common failure mechanisms in subsystems like the RF coil element.

Applicants have developed a new method for performing uniformity measurements that does not require a perfectly uniform region of the phantom, and compensates for signal differences attributable to different compositions or properties of different sections of a phantom. According to this method, the background is sampled in multiple (e.g., hundreds) of regions throughout a three-dimensional volume of the phantom section. These regions are referred to herein as "virtual features" and are identified ahead of time from the design of the phantom as regions where there is known to be nothing but background fill.

Figure 8:
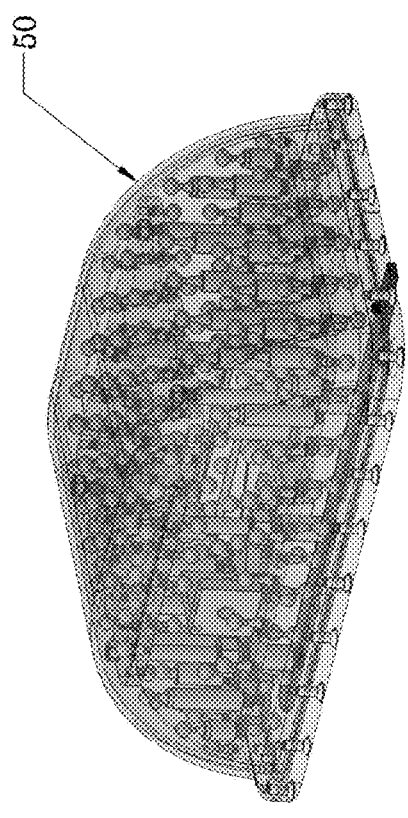
FIG. 8 depicts one section of an aggregate phantom.
Figure 9:
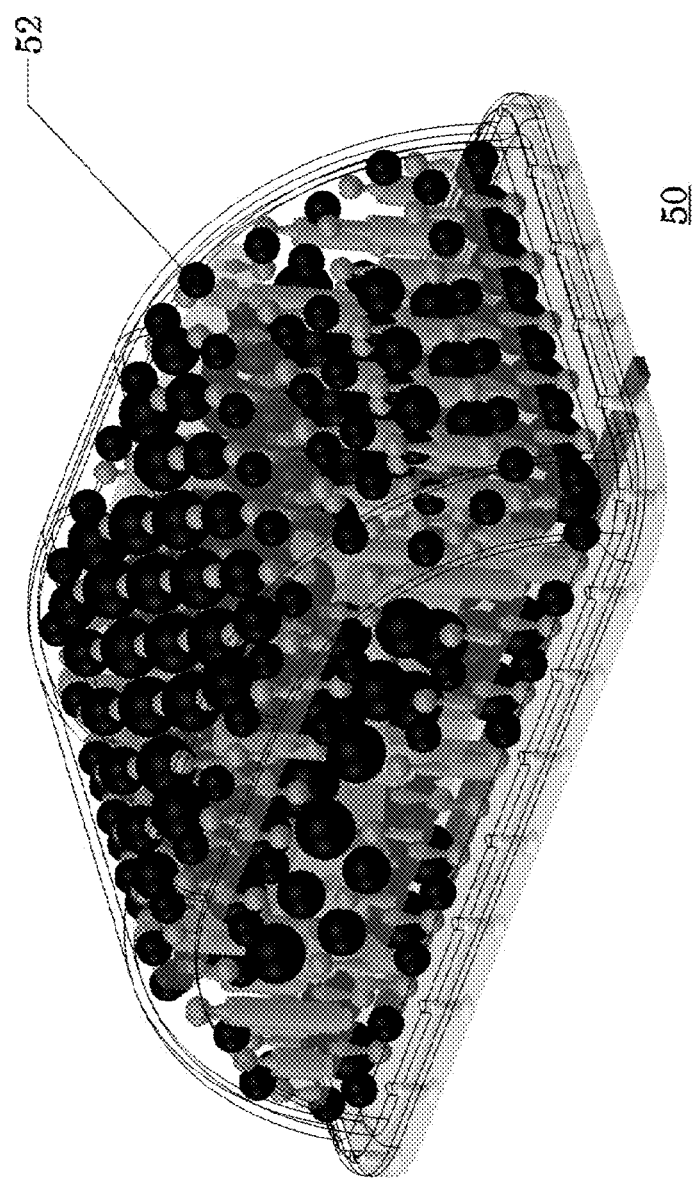
FIG. 9 depicts the attribution of virtual features in the one section of FIG. 8.
Figure 10:
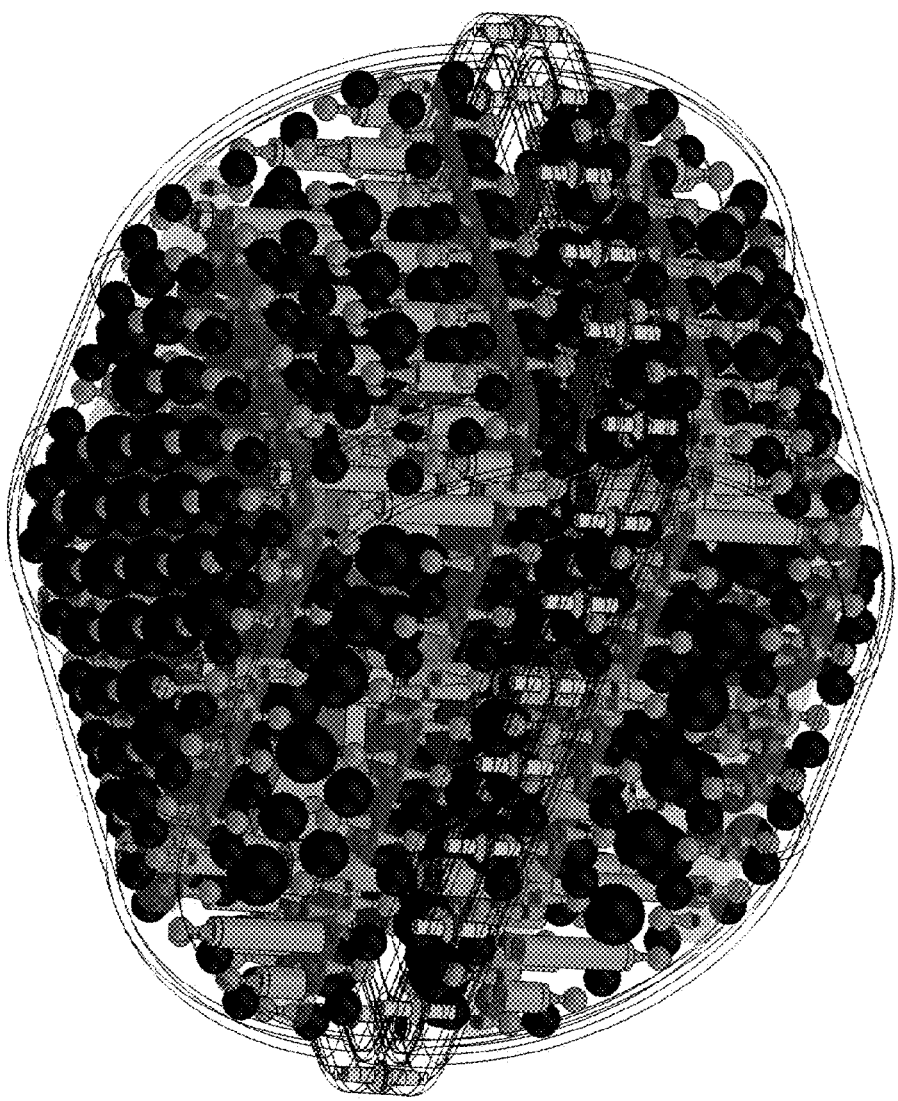
FIG. 10 depicts the attribution of virtual features in an aggregate phantom.

FIG. 8 shows a representative section 50 of an aggregate phantom. In FIG. 9, the attributed locations of spherical virtual features 52 are shown superimposed on section 50. As illustrated in FIG. 10, such virtual features are advantageously attributed to all sections of the aggregate phantom.

The shape, size, distribution, number, and location of the "virtual features" may, of course, vary from that illustrated, provided that each virtual feature corresponds to a region of the section containing only background fill or fluid.

Since the typical signal variations are slowly varying, as long as the sample regions corresponding to the virtual features are taken with sufficiently close spacing to one another, an accurate interpolation can be performed between the samples, and the uniformity characterized everywhere.

The advantages of this technique include:
1. The entire region of the uniformity measurement does not need to be dedicated to the uniformity measurement; it can, advantageously, contain other features.
2. Measurements can be made over entire volumes rather than just a small number of slices in a single slice orientation.

The use of virtual features to measure spatial uniformity of the signal acquired by an imaging system can be applied to a single section or a multi-section phantom. Using a multi-section aggregate phantom introduces a non-ideality that has to be addressed, namely, that each section can, in principle, have slightly different properties that would cause a difference in signal relative to the other sections. This difference could be incorrectly interpreted as a signal non-uniformity.

The method to overcome this potential aberration is related to the methods described above for measuring geometric distortion with multi-section aggregate phantoms. A fit of the signal variation is performed to a function that includes not only continuous, "well-behaved" functions like polynomials, but also includes degrees of freedom associated with each section, such that each section is allowed a signal offset that is uniform within that section.

A fit is then performed to the functions, and the components of the distortion associated with uniform offsets within each section are attributed to differences in the phantom sections rather than true variations of the underlying signal.

The present invention, thus, accommodates not only rigid-body transformations but also differences in the composition or other properties of the sections of an aggregate phantom.

Pursuant to the present invention, to measure spatial uniformity of a signal acquired by an imaging system, a plurality of virtual features is attributed to each section of the aggregate phantom at specified locations containing only background liquid, and a processor may: measure average values within regions of the image corresponding to the virtual features; interpolate between the average values to determine spatial uniformity of a signal acquired by the imaging system, throughout a measurement volume of the phantom; and compensate for any differences in composition between the sections of the aggregate phantom in determining the spatial uniformity of the acquired signal throughout the measurement volume.

Once the signal has been characterized continuously throughout the field of view of the phantom, any desired measurement can be performed. Some examples are the mean, normalized standard deviation, spread, etc.

Figure 11:
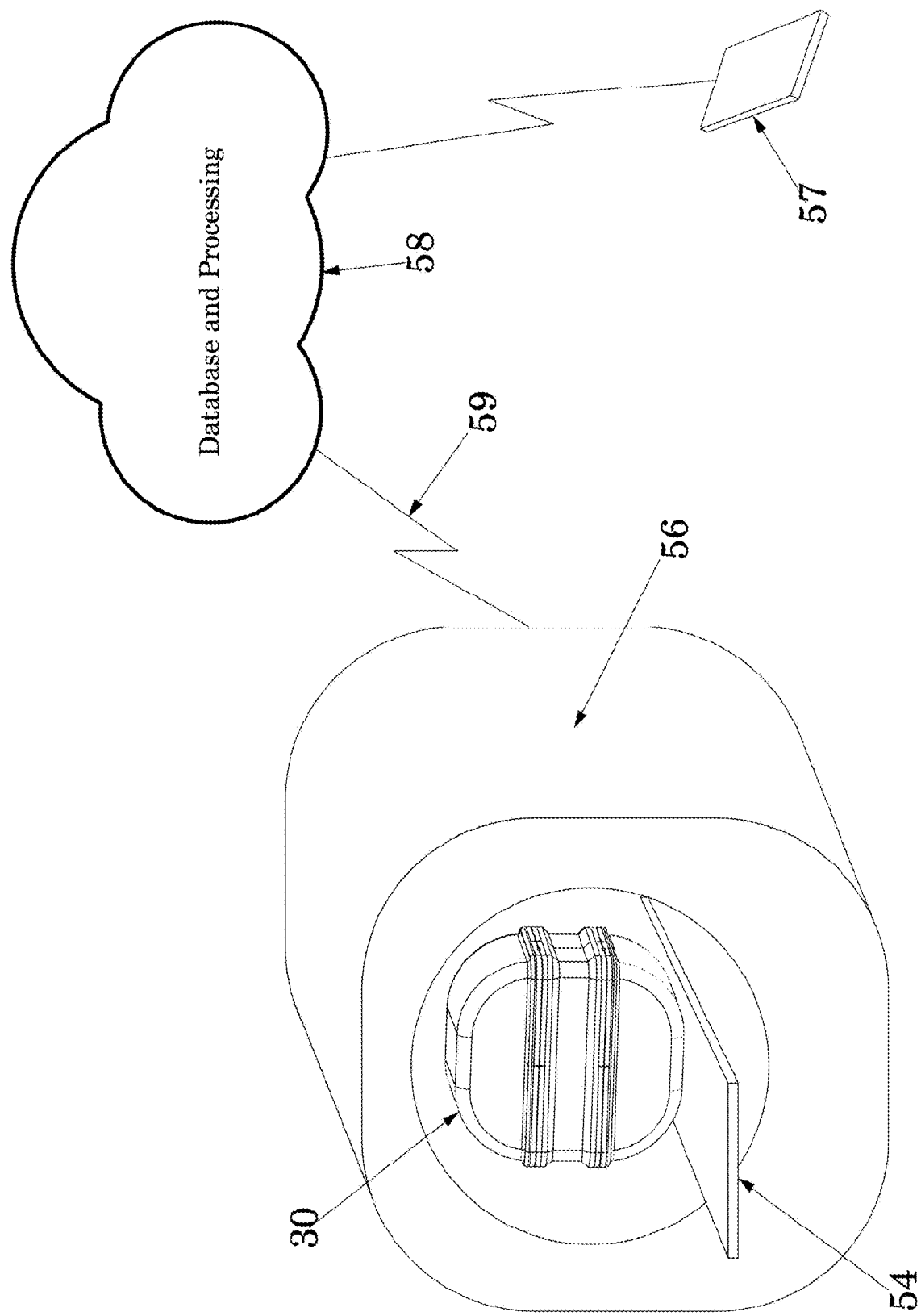
FIG. 11 depicts an online analysis service to implement the methods of this invention.

The various calculations and compensations of the analysis methods of the present invention can be implemented with a programmable processor, either associated with the imaging system or separate therefrom. The analysis may also be provided via an online service such as Image Owl Total QA™ hosted by Image Owl Inc. of Greenwich, N.Y. Such online analysis service is illustrated in FIG. 11, wherein aggregate phantom 30 re-assembled on patient table 54 is imaged by MR imaging system 56, and the image is analyzed, in accordance with the methods of the present invention, by a remote processor 58, and the results, e.g., in the form of a report, are conveyed to a computer, tablet, phone or the like 57, via the internet 59.

The present invention also provides a method for performing geometric distortion measurements, of an imaging system, with a phantom, over a field-of-view larger than an imaging volume of the phantom, even that of an aggregate phantom.

Figure 12A:
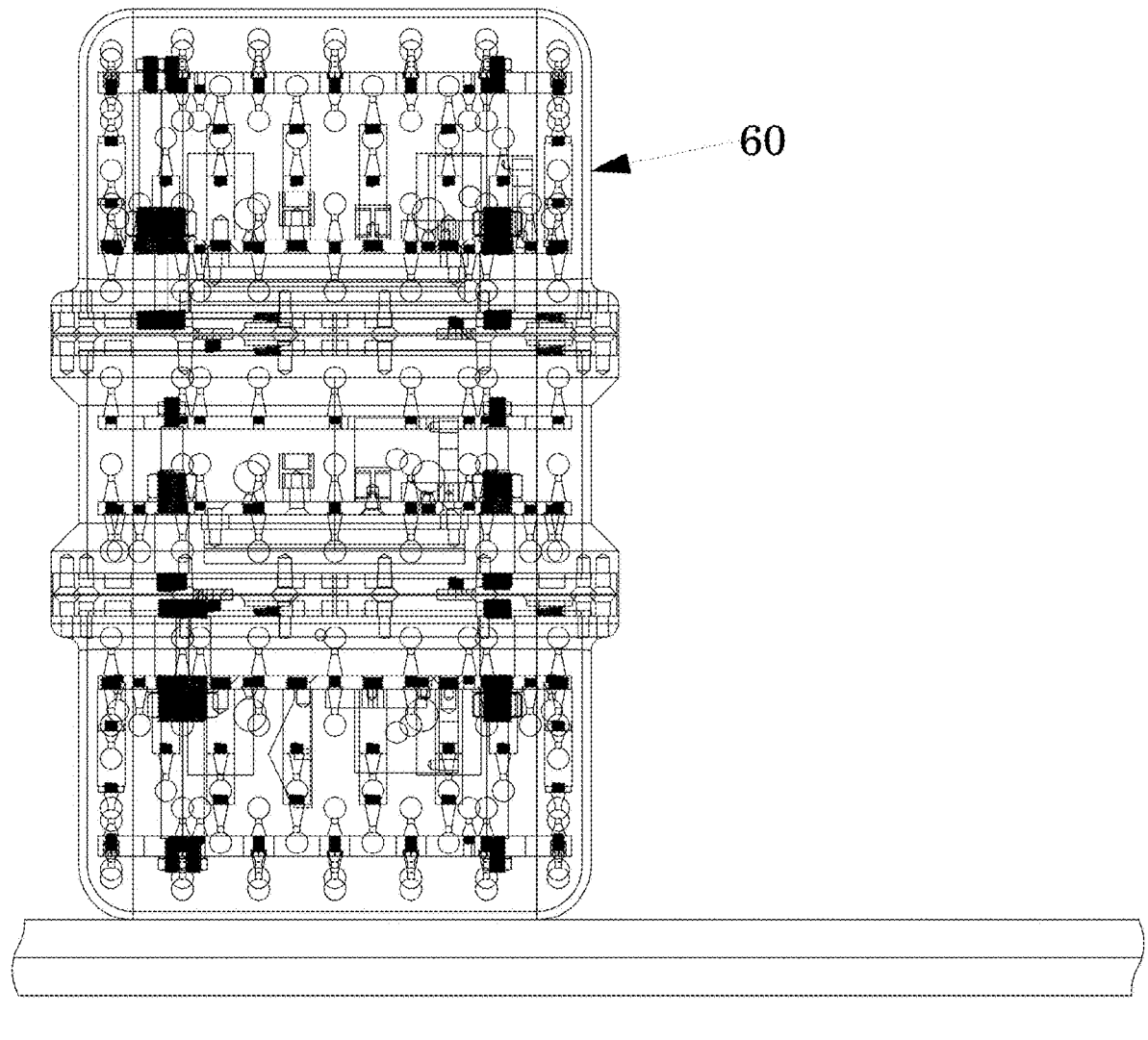
Figure 12B:
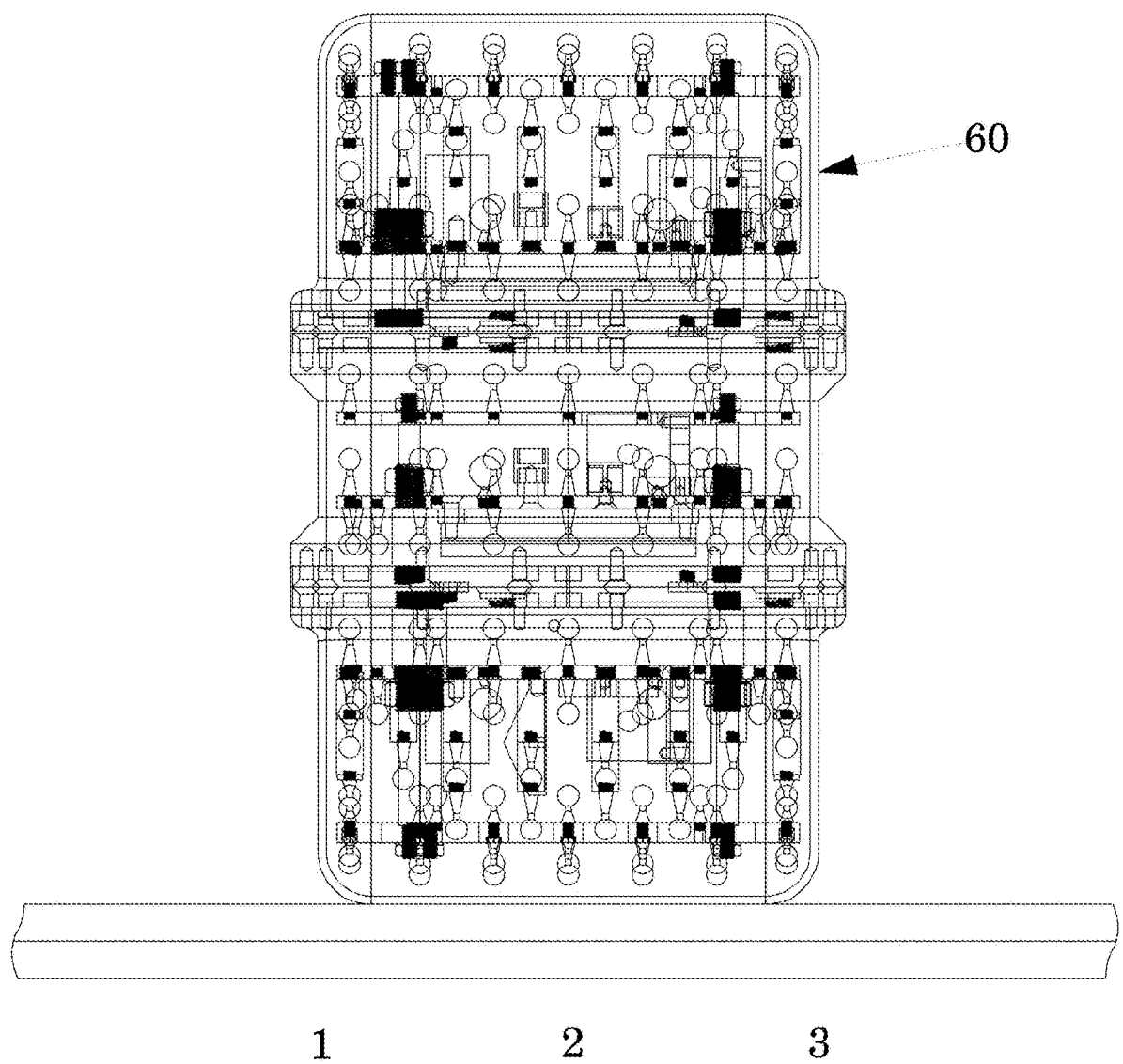
Figure 12D:
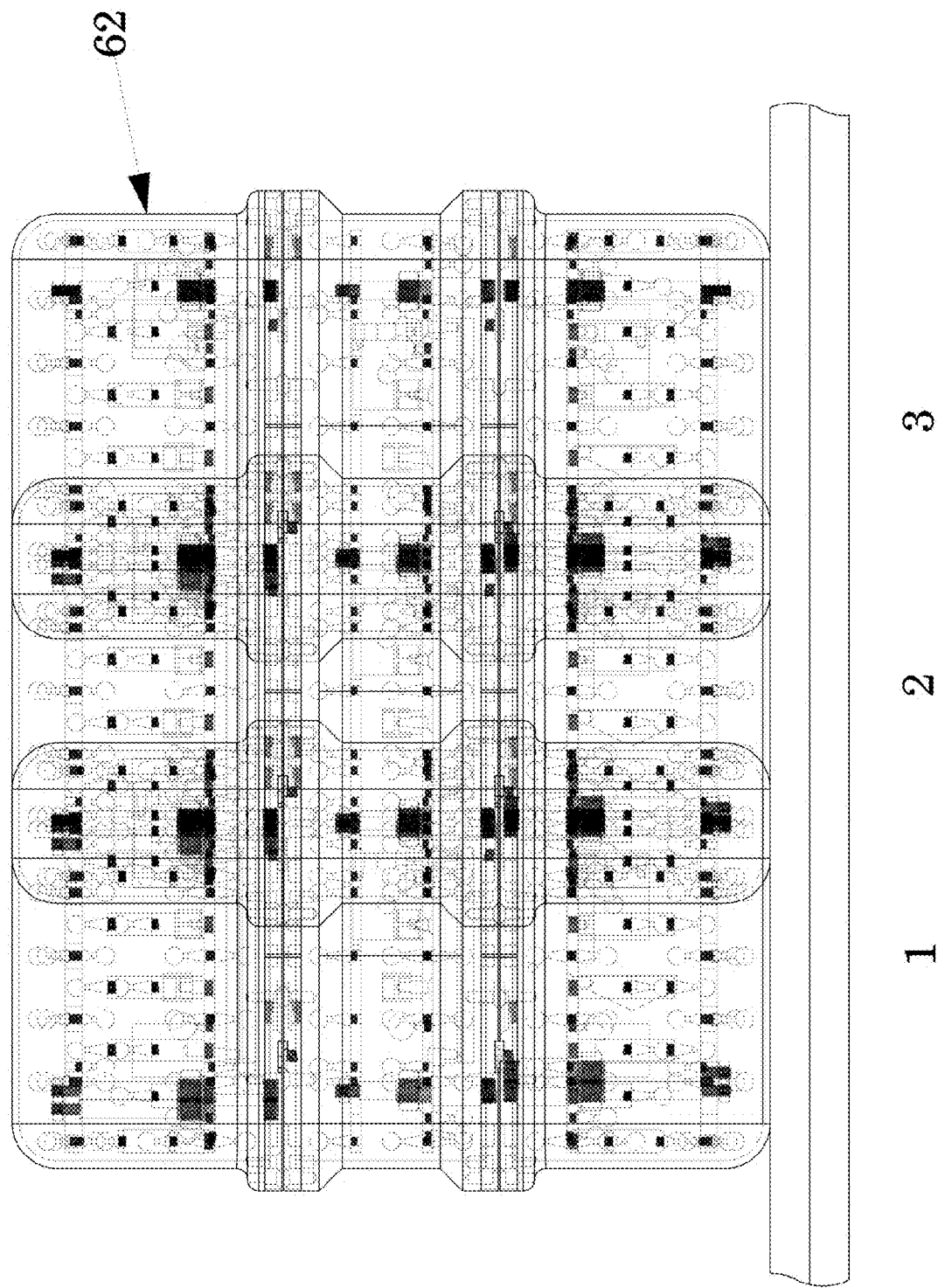

In this method, multiple sets of images are taken of the phantom 60 positioned at multiple locations within the extended field-of-view, by the imaging system. Such repositioning is illustrated in FIGS. 12A, 12B and 12C. This set of images may then be combined to form an extended image as figuratively illustrated in FIG. 12D. A 3D distortion field of the extended image is then determined, and actual geometric distortion of the imaging system is distinguished from rigid-body transformations attributable to repositioning of the phantom, in the distortion field, in a manner similar to that described above for rigid-body transformations attributable to section displacements.

An analysis technique may be employed that takes, as inputs, sets of images with the aggregate phantom (or a standard phantom) scanned in different locations within the imaging system or scanner. In this method, the aggregate phantom is scanned in an initial position and then moved to one or more new locations such that the volume covered by the image scans cover the entire field-of-view of interest. The multiple image scans may or may not overlap. The analysis method then combines these data sets using methods similar to those applied for combining the different individual sections in the aggregate phantom to provide measurements covering the entire field-of-view that is covered by the multiple scans.

Similarly, by moving the phantom relative to the pertinent components of the imaging system, multiple image acquisitions of the phantom can also be combined to provide an extended uniformity measurement in a manner similar to that described above for measuring geometric distortion by repositioning a phantom.

The present invention thus enables precise measurement of geometric distortion over a wide, large or extended field-of-view and precise measurement of spatial uniformity of a signal acquired by the imaging system by using (and optionally repositioning) an aggregate phantom within the imaging system. The aggregate phantom avoids the weight constraints of the prior art while facilitating multiple different measurements with the same aggregate phantom.

The modular design of the aggregate phantom, enables the light-weight phantom sections to be readily handled by a single person without special equipment. The related analysis methods automatically compensate for displacements or varying properties of the phantom sections, or phantom repositioning.

The apparatus and methods of the present invention meet the specific Quality Assurance needs of MR imagers used for MR guided surgery, and radiotherapy planning and guidance where measurement of large field-of-views are required for torso sizes encountered in clinical practice. The present invention facilitates a robust system of quality control for key imaging performance characteristics in order to detect significant deviations before they affect clinical operations and patient outcomes.

The invention claimed is:

1. A method for measuring spatial uniformity of a signal acquired by an imaging system, comprising:
   locating a phantom within the imaging system;
   attributing virtual features to regions at known locations throughout a measurement volume of the phantom, each region containing only background liquid;
   imaging the phantom with the imaging system; and
   with a processor:
      measuring average signals within the regions, and
      interpolating between the average signals to determine spatial uniformity of a signal acquired by the imaging system, throughout a measurement volume of the phantom.

2. The method of claim 1, wherein the phantom comprises an aggregate phantom having a plurality of self-contained sections, the locating comprises separately transporting and re-assembling the sections within the imaging system, the attributing comprises attributing the virtual features to regions in each section, and the processor compensates for any differences in composition between the sections of the aggregate phantom in determining the signal uniformity throughout the measurement volume.

3. The method of claim 2, wherein each virtual feature has a spherical shape.

* * * * *